US008926811B2

(12) United States Patent
Wu

(10) Patent No.: US 8,926,811 B2
(45) Date of Patent: Jan. 6, 2015

(54) DIGITAL MICROFLUIDICS BASED APPARATUS FOR HEAT-EXCHANGING CHEMICAL PROCESSES

(75) Inventor: Chuanyong Wu, Menlo Park, CA (US)

(73) Assignee: Digital Biosystems, Menlo Park, CA (US)

( * ) Notice: Subject to any disclaimer, the term of this patent is extended or adjusted under 35 U.S.C. 154(b) by 716 days.

(21) Appl. No.: 12/666,348

(22) PCT Filed: Jun. 27, 2008

(86) PCT No.: PCT/US2008/068651

§ 371 (c)(1), (2), (4) Date: Nov. 15, 2010

(87) PCT Pub. No.: WO2009/003184

PCT Pub. Date: Dec. 31, 2008

(65) Prior Publication Data

US 2011/0048951 A1 Mar. 3, 2011

Related U.S. Application Data

(60) Provisional application No. 60/946,673, filed on Jun. 27, 2007.

(51) Int. Cl.
*B01L 3/00* (2006.01)
*G01N 33/483* (2006.01)
*B01L 7/00* (2006.01)

(52) U.S. Cl.
CPC ........... *B01L 7/525* (2013.01); *B01L 3/502792* (2013.01); *B01L 2300/0816* (2013.01); *B01L 2300/089* (2013.01); *B01L 2300/1827* (2013.01); *B01L 2400/0427* (2013.01)
USPC ........... 204/411; 204/408; 204/409; 219/483; 422/504

(58) Field of Classification Search
CPC .............. C12N 15/1003; B01L 3/5027; B01L 3/502792; B01L 2400/0427; B81B 2201/058; G01N 33/4833; G01N 33/4836; G01N 33/48707; G01N 33/5302; G01N 33/5308; G01N 33/6875
USPC ......... 204/400–403.03, 408–412, 433, 228.6, 204/230.2, 230.3, 241, 274; 219/209, 219/482–488, 494, 495, 497; 205/775–776, 205/777.5–779, 780–782.5, 783.5, 205/786–787.5, 792–793.5, 794.5; 422/50–504, 507, 509
See application file for complete search history.

(56) References Cited

U.S. PATENT DOCUMENTS 6,113,768 A 9/2000 Fuhr et al.
6,294,063 B1 9/2001 Becker et al.

(Continued)

FOREIGN PATENT DOCUMENTS

EP 1371989 A1 12/2003
EP 1643231 A1 4/2006
WO WO 2006/044966 A1 4/2006

OTHER PUBLICATIONS

PCT International Search Report and Written Opinion, PCT/US2008/068651, Sep. 22, 2008, 6 pages.

(Continued)

*Primary Examiner* — Susan D Leong
(74) *Attorney, Agent, or Firm* — Fenwick & West LLP

(57) ABSTRACT

The present invention provides an apparatus and method for performing heat-exchanging reactions on an electro wetting-based micro fluidic device. The apparatus provides one or multiple thermal contacts to an electro wetting-based device, where each thermal contact controls the part of the electro wetting-based device it communicates with to a designed temperature. The electrowetting-based device can be used to create, merge and mix liquids in the format of droplets and transport them to different temperature zones on the micro fluidic device. The apparatus and methods of the invention can be used for heat-exchanging chemical processes such as polymerase chain reaction (PCR) and other DNA reactions, such as ligase chain reactions, for DNA amplification and synthesis, and for real-time PCR.

11 Claims, 4 Drawing Sheets

(56) References Cited

U.S. PATENT DOCUMENTS

| | | | | |
|---|---|---|---|---|
| 6,911,132 | B2 | 6/2005 | Pamula et al. | |
| 7,163,612 | B2 | 1/2007 | Sterling et al. | |
| 2002/0172969 | A1 | 11/2002 | Burns et al. | |
| 2003/0164295 | A1 | 9/2003 | Sterling | |
| 2003/0173223 | A1 | 9/2003 | Gascoyne et al. | |
| 2004/0055891 | A1 | 3/2004 | Pamula et al. | |
| 2004/0211659 | A1 | 10/2004 | Velev | |
| 2007/0141593 | A1 | 6/2007 | Lee et al. | |
| 2007/0241068 | A1 * | 10/2007 | Pamula et al. | 210/806 |
| 2008/0169197 | A1 | 7/2008 | McRuer et al. | |

OTHER PUBLICATIONS

Chinese Office Action, Chinese Application No. 200880016986.4, Feb. 24, 2011, 15 pages.

European Extended Search Report, European Application No. 08754752.7, Feb. 14, 2011, 6 pages.

Fan, S-K. et al., "Manipulation of Multiple Droplets on NxM Grid by Cross-Reference EWOD Driving Scheme and Pressure-Contact Packaging," IEEE, 2003, p. 694-697.

Moesner, F.M. et al., "Devices for Particle Handling by an AC Electric Field," Proceedings of the Workshop on Micro Electrical Mechanical Systems, IEEE, Jan. 29, 1995, pp. 66-71.

PCT International Search Report and Written Opinion, PCT Application No. PCT/US08/006709, Aug. 19, 2008, 7 pages.

Chinese Office Action, Chinese Application No. 200880016986.4, Nov. 2, 2011, 6 pages.

Chinese First Office Action, Chinese Application No. 200880015181.8, Jun. 1, 2012, 10 pages.

European Examination Report, European Application No. 08754752.7, May 13, 2013, 5 pages.

Chinese Second Office Action, Chinese Application No. 200880015181.8, Apr. 18, 2013, 10 pages.

Chinese Office Action, Chinese Application No. 200880015181.8, Feb. 20, 2014, 12 pages.

Korean Office Action, Korean Application No. 10-2009-7027004, May 19, 2014, 9 pages.

* cited by examiner

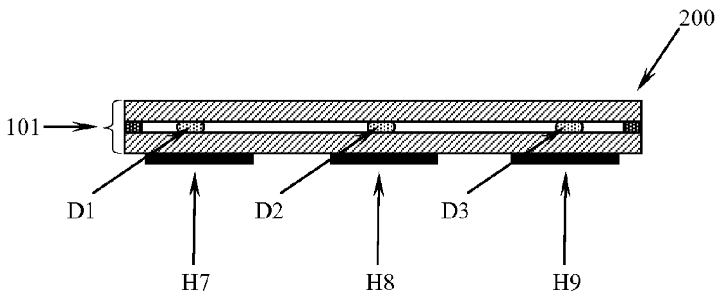
FIG. 2A
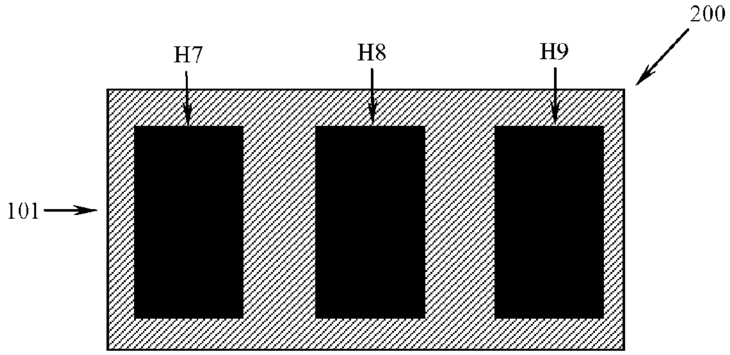
FIG. 2B
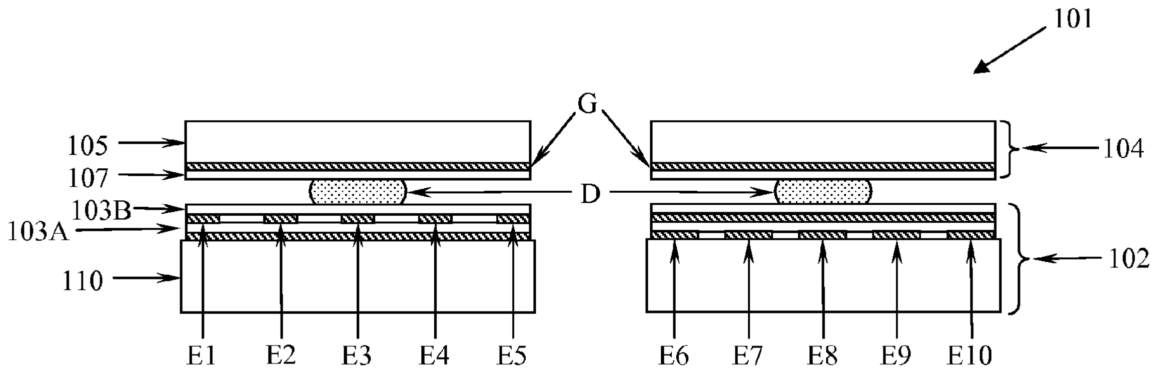
FIG. 3A
FIG. 3B

DIGITAL MICROFLUIDICS BASED APPARATUS FOR HEAT-EXCHANGING CHEMICAL PROCESSES

CROSS-REFERENCE TO RELATED APPLICATIONS

This application is the National Stage of and claims priority from International Application No. PCT/US2008/068651, filed Jun. 27, 2008, and claims the benefit of U.S. Provisional Application No. 60/946,673, filed Jun. 27, 2007, both of which are incorporated by reference in their entirety.

TECHNICAL FIELD

The present invention relates generally to the field of molecular biology, and relates to methods for amplifying nucleic acid target sequences in droplet-based microfluidic devices. It particularly relates to polymerase chain reaction and isothermal amplification in/on droplet-based microfluidic devices. The present invention also relates to methods of detecting and analyzing nucleic acid in droplet-based microfluidic devices.

Introduction

During the last two decades or so, polymerase chain reaction (PCR) has radically changed the scientific world. This technique amplifies minute quantities of DNA or RNA so that, for example, they can be detected and analyzed. PCR technique has been applied in many different fields. Examples include testing viral load, quantifying food borne pathogens, clinical diagnosis, drug resistance analysis and forensic science. Using PCR technology, physicians and researchers can identify the source of a viral infection by analyzing one single sperm cell. The infectious organisms can now be detected using PCR are HIV-1, Hepatitis B, Hepatitis C, SARS virus, West Nile virus, Mycobacterium tuberculosis, etc.

As a well-established procedure, PCR requires the repetition of heating and cooling cycles, in order to repeat the denaturation, annealing and extension processes, in the presence of an original DNA target molecule, specific DNA primers, deoxynucleotide triphosphates, and thermal-stable DNA polymerase enzymes and cofactors. Each temperature cycle doubles the amount of target DNA sequence, leading to an exponential accumulation of the target sequence.

A PCR procedure typical involves: 1) processing of the sample to release target DNA molecules into a crude extract; 2) addition of an aqueous solution containing enzymes, buffers, deoxyribonucleotide triphosphates (dNTPs), and oligonucleotide primers; 3) thermal cycling of the reaction mixture between two or three suitable temperatures, for example, 90-98° C., 72° C., and 37-55° C.; and 4) detection of the amplified DNA. At the end of PCR cycle, the target sequence can be amplified by a factor of 1,000,000 to 1,000,000,000, making the detection of the target sequence easier and more accurate.

So, it is very important to be able control the temperature accurately and cycle the temperatures in a timely fashion. Many methods have been utilized to achieve PCR temperature cycling—air cyclers, metal heating blocks, water baths, etc. Many commercial PCR instruments exist too. All of them suffer limitations in term of amount of reagent usage, temperature cycle time, data quality, operation easiness and cost-effectiveness.

Recently, microfluidic systems have been gaining increasing interests in many fields and especially in chemical and biochemical related applications. Mature semiconductor manufacturing techniques such as photolithography and wet chemical etching and polymer processing techniques such as injection molding and hot embossing have helped tremendously in the design and fabrication of microfluidic systems.

Microfluidic systems have been used in chemical reaction and synthesis, liquid chromatography, capillary electrophoresis, PCR, and many other fields, because of the reduced reagent consumption and integration easiness. PCR has been done on droplet-based microfluidic chips [Pollack, M. G. et al, uTAS 2003], as well as channel-based microfluidic chips [Kopp, M. et al, Science 1998, 280, 1046-1048]. Patents (for example WO 2006/124458 and US 2008/0038810) have been filed to present ideas for carrying out temperature related biochemical or chemical reactions utilizing some electrowetting based devices. Presented here is an improved method of realizing temperature cycling of reagents, which is an important step in PCR, utilizing a digital microfluidic device that is based on the two-sided electrode control architecture presented in the co-owned U.S. Provisional Patent Application No. 60/940,020.

As described in detail in the pending and co-owned U.S. Provisional Patent Application No. 60/940,020, filed on May 24, 2007, droplet-based microfluidic systems offer many advantages over channel-based microfluidic systems in general, such as reconfigurability and control easiness. When performing PCR on a channel-based system, such as the one mention above [Kopp, M. et al, Science 1998, 280, 1046-1048], unwanted bubble creation can clog channels, thereby terminating the experiment. Also dispersion of the reagent slugs can have non-linear effect for signal detection. When performing PCR on a droplet-based system, the reagents are dispensed as droplets and the droplets go through temperature cycling. This immediately reduces the chances of having the two serious problems commonly encountered in a channel-based microfluidic system—bubble and dispersion, as it's very unlikely to have bubbles, if created, to stay inside the droplets, and all reagents within a droplet stay together all the time so that dispersion effect is negligible. Comparing to the single control electrode layer device architectures in patents WO 2006/124458 and US 2008/0038810, the dual-control-electrode-layer two-sided electrode control device architecture presented in the U.S. Provisional Patent Application No. 60/940,020 has the advantage of using less number of control electrodes to provide a two dimensional array of similar number of droplet activation sites. The implication of utilizing the said dual-control-electrode-layer device architecture is lower device manufacturing cost and easier control instrument design, among other things, comparing to the single-layer control electrodes described in patent applications WO 2006/124458, US 2008/0038810, and U.S. Pat. No. 6,911,132, etc. For many applications, cost-effectiveness and easy-to-use are often times two of the most important factors that users consider when choosing a device.

The apparatus of the present invention is designed to use with an above mentioned electrowetting-based device. The apparatus enables temperature cycling by controlling different areas/portions of the electrowetting-based microfluidic device to different temperatures and by moving the liquid in the form of droplets to the different temperature zones using electrowetting techniques.

To divide an electrowetting-based device to different zones and control the zones to different temperatures individually offers many advantages. First, less energy is needed comparing to the method which cycles the whole device through different temperatures, because once the zones reached their temperature set-points, only small amount energy is needed to maintain the temperature set-points. This makes it easier to design a smaller control setup/system. Second, comparing with the method to cycle the whole device, the time it takes for the reagent to change from one temperature to another can be shorter in present invention. In this invention, a droplet can be transported from one temperature zone to another rapidly and it reaches thermal equilibrium with a temperature zone very quickly due to its small size. This is particularly desirable for rapid-cycle PCR, in which it was found that rapid temperature cycling with minimal annealing and denaturation times improves quantitative PCR (see for example, Wittwer, C. T. et al, Methods 2001, 25, 430-442). When trying to temperature cycle the whole device, things can make it difficult to have faster cycle time—1.) it takes time for the heat to propagate from the temperature control elements to the liquid in the middle; 2.) certain thermal inertia of the device can also limit how fast the whole device can be temperature cycled; 3.) temperature cycling the whole device puts the whole device under repeated thermal shocks, which can cause possible features such as thermal bonding and hydrophobic coating on the device to fail. This puts more burdens on manufacturing to make reliable devices, which in turn pushes manufacturing cost higher.

SUMMARY

The present invention provides apparatus and methods for temperature cycling, for amplification of nucleic acids, such as PCR and isothermal amplification of DNA, and for detection of PCR related signal as detection area can be allocated on the electrowetting-based device and liquid droplets can be moved to the detection area by electrowetting techniques. The methods of the invention have the advantage of permitting signal detection at each temperature cycle. Therefore, the invention provides apparatus and methods for real-time quantitative PCR, which is based on the change in fluorescence associated with the accumulation of amplification products and to monitor the fluorescence change in real time during temperature cycling. Fluorescence changes may be attributed to double-stranded DNA binding dyes such as SYBR Green or probe based chemistries such as TaqMan®, Molecular Beacons, Scorpions™, etc.

Melting curve analysis is an assessment of the dissociation-characteristics of double-stranded DNA during heating. The information gathered can be used to infer the presence of and identity of single nucleotide polymorphisms. The present invention provides methods for implementing temperature sweeps needed for melting curve analyses. In one aspect, the invention provides methods to implement temperature changes through spatial variation. Thus, two or more regions of the device can be set to different temperatures (proper for melting curve analysis), at thermal equilibrium, a path (or multiple paths) of continuous temperature change from the temperature at the highest temperature region to the temperature at the lowest temperature region can be designed on the device. A droplet of PCR product can be moved along this path (or paths), and the fluorescence measured as the PCR product moves along the path. The change in fluorescence can be used to obtain the melting curve for the DNA strand. In another aspect of the invention, the droplet of PCR product can be made to remain stationary at one location and the temperature(s) at the location can be changed. As described above, the fluorescence measurement can be performed at the location to obtain the melting curve for the DNA strand.

In yet another aspect, the invention provides methods for nucleic acid amplification such as PCT and isothermal target amplifications methods, such as SDA (strand displacement amplification), NASBA (nucleic acid sequence based amplification), TMA (transcription-mediated amplification), RCA (rolling-circle amplification, LAMP (loop-mediated amplification) and HDA (helicase-dependent amplification), can perform DNA or RNA amplifications at one temperature. Thus, the present invention provides apparatus and methods for isothermal amplifications, and multiple isothermal amplifications at different temperatures that can be performed simultaneously on the device described in this invention. In one aspect of the invention, as few as one heater is needed to control a specified region of the device to a specified temperature, a droplet of DNA target can be transported to this region to carry out an isothermal amplification. Optionally, droplets with negative and/or positive controls can be transported to different positions in this temperature region at the same time. In another aspect of the invention, with the use of multiple heaters to provide different temperature regions on the device, simultaneous multiple isothermal amplifications can be performed by transporting the DNA targets to different locations which are at different temperatures. The progress of the isothermal amplification can be followed and quantitated using fluorescence detection, as described for real-time quantitative PCR above.

The apparatus and methods of the invention can be used for the detections of RNAs and proteins as well. For example, with this invention, real time RT-PCR (Reverse Transcription-Polymerase Chain Reaction) can be used for RNA detections, and real time immuno-PCR can be used to detect proteins. Of course, this invention can facilitate IRSG (Isothermal RNA Signal Generation)—isothermal RNA amplification and detection without converting RNA to DNA before any specific detection reaction. Also, this invention supports isothermal protein detections such as IAR (Isothermal Antibody Recognition). Indeed, with this invention, it is possible to design low cost portable devices (and instruments), and each device provides the capabilities of detecting a set of DNAs, RNAs and proteins, etc.

BRIEF DESCRIPTION OF THE DRAWINGS

FIG. 2A is a cross-sectional view of a temperature control mechanism of an electrowetting-based device, which has temperature control elements thermally communicating with the device only from one side, in accordance with the present invention.

FIG. 2B is the top view of FIG. 2A from the heaters' side.

FIGS. 3A and 3B are two cross-sectional views, 90 degrees relative to each other, of an electrowetting microactuator mechanism having a two-sided electrode configuration in accordance with the present invention.

DETAILED DESCRIPTION OF THE INVENTION

For purposes of the present disclosure, the term "microfluidic" refers to a device or system having the capability of manipulating liquid with at least one cross-sectional dimension in the range of from a few micrometers to about a few hundred micrometers.

For purposes of the present disclosure, the term "communicate" is used herein to indicate a structural, functional, mechanical, electrical, optical, thermal, or fluidic relation, or any combination thereof, between two or more components or elements. As such, the fact that one component is said to communicate with a second component is not intended to exclude the possibility that additional components may be present between, and/or operatively associated or engaged with, the first and the second component.

For purposes of the present disclosure, it will be understood that when a liquid in any form (e.g., a droplet or a continuous body, whether moving or stationary) is described as being "on", "at", or "over" a surface, electrode, array or device, such liquid could be either in direct contact with surface/electrode/array/device, or could be in contact with one or more layers or films that interposed between the liquid and the surface/electrode/array/device.

As used herein, the term "reagent" describes any agent or a mixture of two or more agents useful for reacting with, diluting, solvating, suspending, emulsifying, encapsulating, interacting with, or adding to a sample agent. A reagent can be living such as a cell or non-living. Reagents for a nucleic acid amplification reaction include, but not limited to, buffer, polymerase, primers, template nucleic acid, nucleotides, labels, dyes, nucleases, and so on.

Figure 1A:
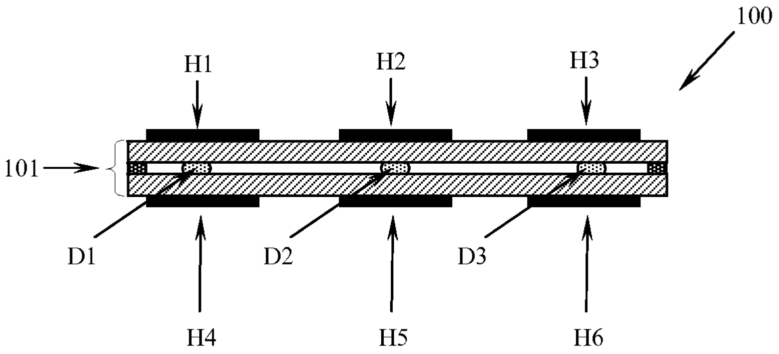
FIG. 1A is a cross-sectional view of a temperature control mechanism of an electrowetting-based device, which has temperature control elements making thermal communication with the device both on the top and on the bottom, in accordance with the present invention.
Figure 1B:
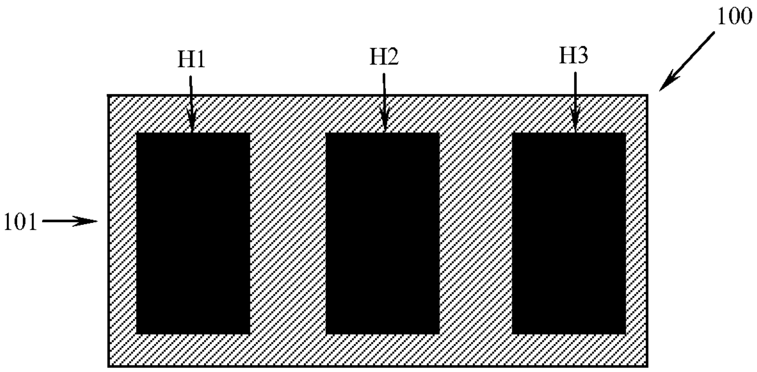
FIG. 1B is the top view of FIG. 1A.
Figure 1C:
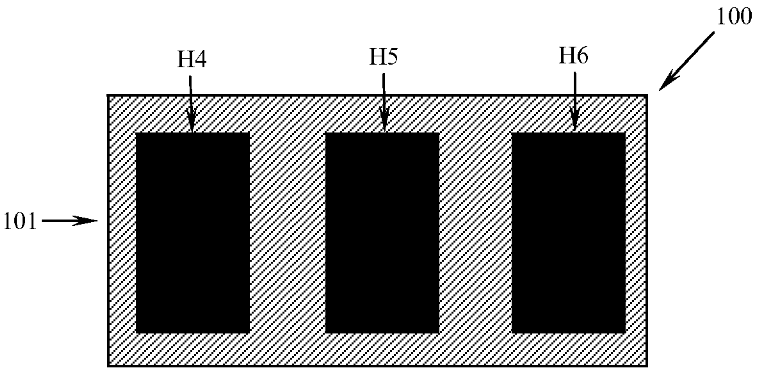
FIG. 1C is the bottom view of FIG. 1A.

Referring now to FIGS. 1A to 1C, electrowetting-based device of the invention, designated 100, is used for effecting droplet temperature control. Droplets D1, D2 and D3 are electrolytic, polarizable, or otherwise capable of conducting current or being electrically charged. In this embodiment, electrowetting-based device 101 is sandwiched between upper temperature control elements, generally designated H1, H2 and H3, and lower temperature control elements, generally designated H4, H5, and H6. The terms "upper" and "lower" are used in the present context only to distinguish these two planes H1/H2/H3 and H4/H5/H6, and not as a limitation on the orientation of the planes H1/H2/H3 and H4/H5/H6 with respect to the horizontal. In this embodiment, the goal is to control the three regions in device 101 that droplets D1, D2 and D3 might make contact with to three different temperatures by controlling the six temperature control elements H1, H2, H3, H4, H5, and H6. This implies that the temperatures of the top inner surface and the bottom inner surface that the droplet (D1, D2 or D3) touches should substantially close.

Referring now to FIGS. 2A and 2B, another embodiment of the invention electrowetting-based device, designated 200, is illustrated for effecting droplet temperature control. Droplets D1, D2 and D3 are electrolytic, polarizable, or otherwise capable of conducting current or being electrically charged. In this embodiment, three temperature control elements H7, H8 and H9 are designed to make thermal contacts with electrowetting-based device 101. In this embodiment, the goal is to control the three region of the bottom plate of device 101 that droplets D1, D2 and D3 make contact with the three different temperatures by controlling the three temperature control elements H7, H8, and H9

A droplet described in this invention is sandwiched between two plates with a gap of typically less than 1 mm. In the first embodiment, the droplet will generally quickly equilibrate with the temperature of the part of the device it makes contact with once transported there, as the temperatures of the upper and lower plates where the droplet makes contacts with are substantially close. In the second embodiment, where the temperature of the top plate is generally different from the temperature of the bottom plate, the temperature of the droplet, once transported and thermally equilibrated with the device, will settle to a value that is between the two temperature values.

The temperature of a controlled region of an electrowetting-based device can range from −20° C. (minus 20° C.) to 200° C., and preferably from 0° C. to 120° C., and more preferably from 37° C. to 95° C.

The temperature control elements H1 to H9 can be implemented in the apparatus using any of the means known in the art. Peltier devices, also known as thermoelectric coolers (TE or TEC), are preferred for use in this invention because of their capabilities to do both heating and cooling. Resistive (also called Resistance) heaters can also be used here combined with natural or forced convection cooling when needed. The temperature control elements can make contact with the electrowetting-based device with or without intervening components. As usual practices, materials like thermo grease and thermo foam can be often used to improve the thermal contact between the temperature control elements and the electrowetting-based device.

The temperature control elements are not limited to the ones described hereinabove, and the shapes can be different too. Many other apparatuses and/or methods can serve temperature control purposes. For example, H1 to H9 can be tubes where temperature can be controlled using water or air flowing within the tubes, where the water or air are at the desired temperature. Temperature control capabilities of H1 to H9 can also be achieved by thermal radiation making heat transfer with the electrowetting-based device with or without intervening components placed between the device and the thermal radiation source.

In one aspect of the invention, the temperature control elements can be integral part of the electrowetting-based device. One example of this implementation, but not limited to, is to attach thin film resistive (resistance) heaters to the device. Although this will make the cost of making the electrowetting-based device higher due to the extra heaters, the temperature control can be more consistent as it includes the heaters to be part of the device manufacturing process.

As will be evident to one of skill in the art, the apparatus 100 described in FIGS. 1A-1C, and apparatus 200 describes in FIGS. 2A and 2B can be placed in a thermal controlled environment to improve temperature control efficiency.

In another aspect, the temperature control elements can be integrated with feedback control. Temperature measurement devices/tools such as, but not limiting to, thermal couple, thermistor and resistance temperature detector (RTD) can be used to continuously monitor the temperature of the device. They can be embedded in the space between, but not limited to, the top plate and the bottom plate of the device temporarily for temperature calibration or permanently to enable closed-loop temperature control during run-time. As will be evident to one of skill in the art, the use of a proper material (for example platinum) allows some of the droplet control electrodes to simultaneously function as resistance temperature detector(s) for temperature measurement purposes.

As mentioned earlier, the amount of power needed to maintain the temperatures of the device can be very small. This low power requirement characteristic makes it possible to build the apparatus into a battery operated handheld systems for use in areas where access to electricity is difficult or impossible. This invention thus finds use in applications to point-of-care (POC) healthcare testing, and can tremendously improve quality of life by its use in disease prevention and treatment.

FIGS. 3A and 3B are the detailed cross-sectional views of the electrowetting-based device 101 shown in FIGS. 1A and 2A. In this embodiment, droplet D is sandwiched between a lower plate, generally designated 102, and an upper plate, generally designated 104. The terms "upper" and "lower" are used in the present context only to distinguish these two planes 102 and 104, and not as a limitation on the orientation of the planes 102 and 104 with respect to the horizontal. Plate 102 comprises two elongated arrays, perpendicular to each other, of control electrodes. By way of example, two sets of five control electrodes E (specifically E1, E2, E3, E4, E5, E6, E7, E8, E9 and E10) are illustrated in FIGS. 3A and 3B. It will be understood that in the construction of devices benefiting from the present invention, control electrodes E1 to E10 will typically be part of a larger number of control electrodes that collectively form a two-dimensional electrode array or grid.

Figure 4:
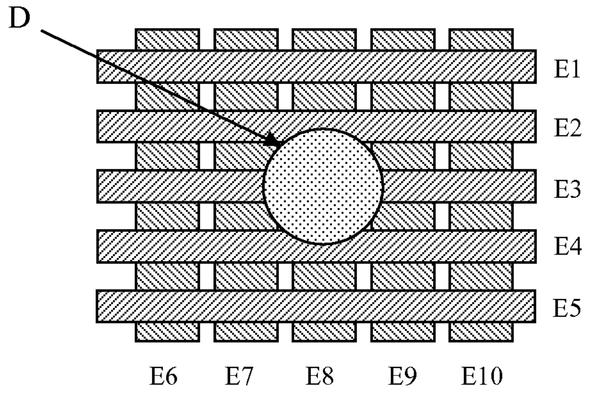
FIG. 4 is a top plan view of the control electrodes embedded on the substrate surface.

FIG. 4 is a top plan view of the control electrodes embedded in the lower plate of an electrowetting-based devices used in this invention, designated 102 in FIGS. 3A and 3B. A droplet D is shown for illustration purposes.

Figure 5:
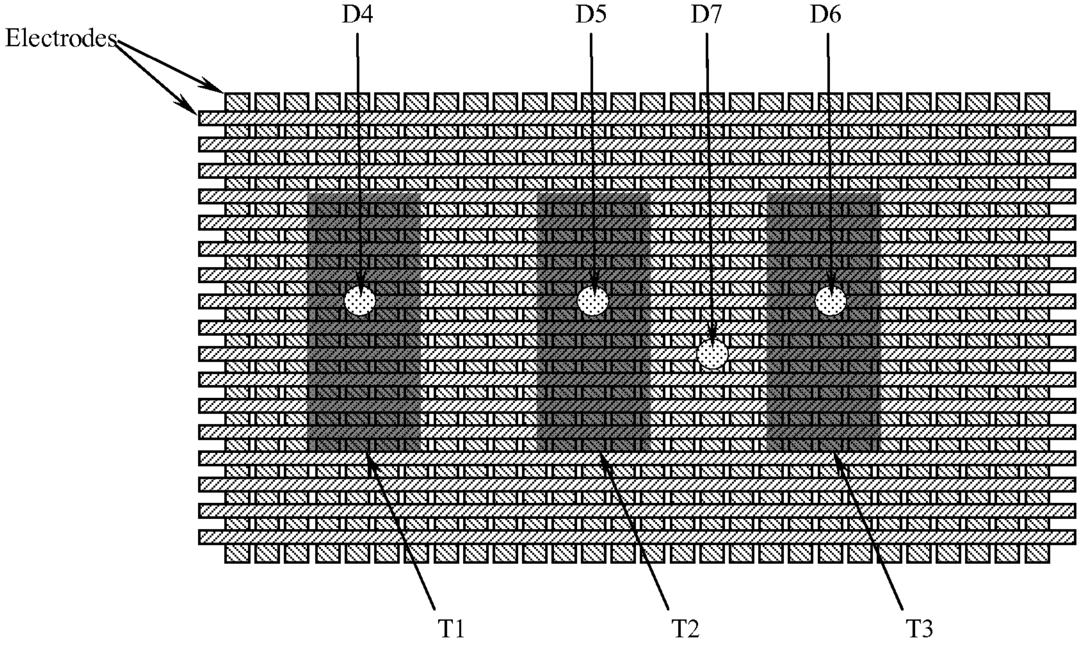
FIG. 5 is a schematic view of different droplets at different temperature zones at the same time or the same droplet at different temperature zones at different times.

FIG. 5 illustrates the temperature control mechanism of an electrowetting-based device. Three zones on the electrowetting-based devices can be controlled at temperatures T1, T2 and T3, by using the temperature control elements H1 to H9 described in FIGS. 1A through 2B. D4, D5 and D6 are three droplets transported to the three temperature zones T1, T2 and T3, respectively, and D7 is situated at another position in the device. The droplets D4, D5, D6 and D7 can have different compositions, or they can be from the same sample, where the sample can be divided into different droplets and each droplet individually transported to a different position on the device at different times.

Figure 6:
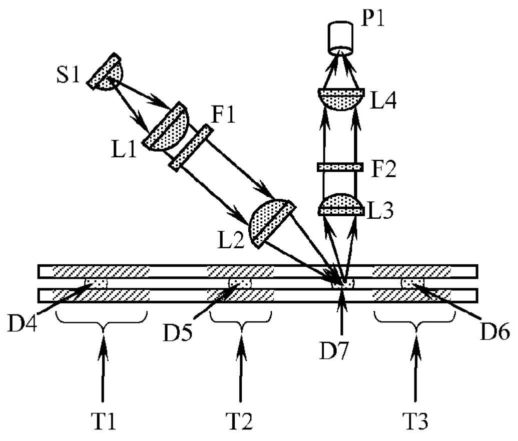
FIG. 6 illustrates the signal excitation and detection of the droplets in an electrowetting-based temperature control apparatus in accordance with the present invention.

FIG. 6 demonstrates the signal detection capability associated with the thermal control apparatus described in this invention. It demonstrates a light induced fluorescence measurement of a droplet, where the targeted molecule absorbs the excitation light and goes to higher but unstable energy state. After certain time delay, the excited molecule goes back lower energy state by releasing the extra energy. One way to release the extra energy is by emitting photons or fluorescing; and we can use fluorescence measurement in this application to gain insight into the targeted molecule. In FIG. 6, Light emitted from LED S1 is collected and collimated by lens L1. Filter F1 is used to limit the bandwidth of the excitation light for the experiment. Lens L2 is used to focus the excitation light onto the target droplet. Fluorescence signal coming from the target droplet is collected and collimated by lens L3. Filter F2 is used to get rid of unwanted light such as the stray light or fluorescence that is not coming from the droplet. Lens L4 is used to focus the collected fluorescence on to the photodiode P1 for detection purposes. FIG. 6 uses one excitation source S1 and one detector P1. This does not limit the use of multiple excitation sources and multiple detectors. For example, light from two or more LEDs with different wavelengths can be collimated, filtered and combined into one beam of light using dichroic mirrors and/or regular mirrors and then focused on to the targeted droplet using a focus lens; the fluorescence light coming out from the targeted droplet can be collected and collimated using a lens, and the collimated light can be split into different beams of light of different wavelengths using dichroic mirrors and/or regular mirrors and then focused into different photodiodes using different lenses and filters.

The excitation source is not limited to just LEDs, but can include other excitation sources, such as discharge lamps and halogen lamps. The detection device can be a photodiode Charge Coupled Devices (CCD), photo-multiplier tubes (PMT), or any other detection device.

The detection with electrowetting-based temperature control apparatus described in this invention can be light induced fluorescence measurement, or any other detection method. Other detection methods include, but not limited to, Raman scattering measurement, fluorescence polarization detection, and fluorescence resonance energy transfer investigation.

EXAMPLE 1

Droplet-Based Real-Time PCR

Figure 7:
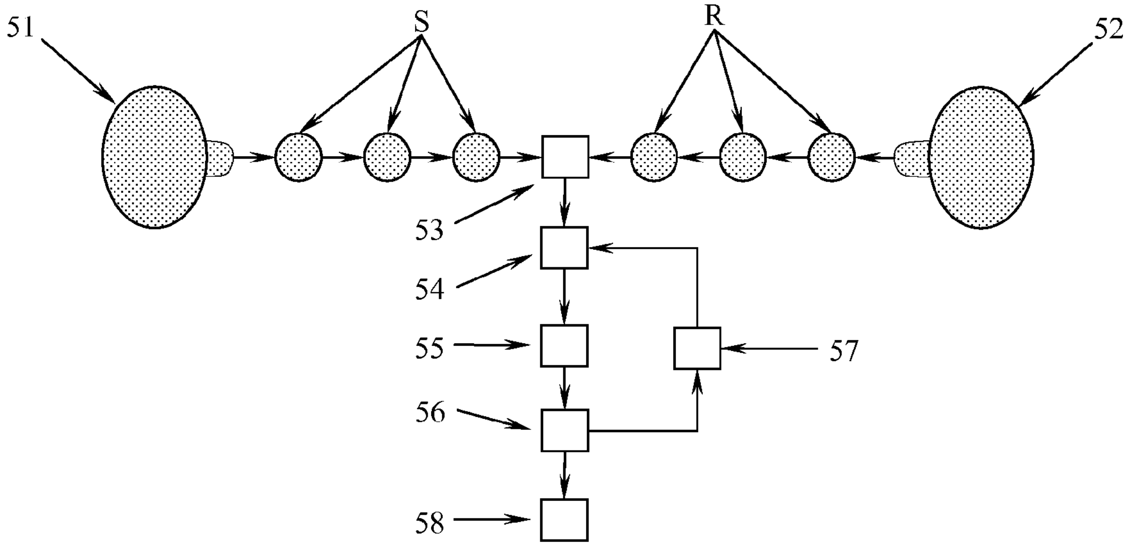
FIG. 7 illustrates the methods of the invention where the droplets from different liquid sources are mixed together, transported periodically to different temperature zones in an electrowetting-based device. Signal measurement is done at every temperature cycle.

Referring now to FIG. 7, a method for 1) dispensing droplets from sample reservoir 51 and PCR premix reservoir 52 on an electrowetting device; 2) mixing the sample droplets with the buffer droplets; 3) periodically moving the mixed droplets to the three temperature zones and performing signal excitation and detection at each cycle. Sample droplets S typically contain a targeted DNA molecule of interest (a known molecule whose concentration is to be determined by real-time PCR). PCR premix contains PCR buffer, oligonucleotide primers, dNTPs and Taq DNA polymerase. The several sample droplets S shown in FIG. 7 represent either separate sample droplets that have been discretized from reservoir 51, or a single sample droplet S movable to different locations on the electrowetting device over time and along various flow paths available. Similarly, the several PCR premix droplets R shown in FIG. 7 represent either separate PCR premix droplets that have been discretized from reservoir 52, or a single PCR premix droplet movable to different locations on the electrowetting device over time and along various flow paths available.

Functional region 53 is a mixer where sample droplets S and PCR premix droplets R are combined together. Functional regions 54, 55 and 56 are the three temperature zones for PCR reaction to take place. Functional region 57 is for signal excitation and detection of a targeted droplet. Finally, functional region 58 is a storage place where droplets are collected after detection and/or analysis are complete.

Functional regions 54, 55, 56 and 57 together enable PCR temperature cycling and signal detection of a droplet. A targeted droplet, which is typically a mixture of the sample and the PCR premix, is transported to functional regions 54, 55, 56 and 57 in a designed sequence and time to go through temperature cycling for PCR and signal detection at each temperature cycle. After desired number of temperature cycles, the droplet is transported to functional region 58 for disposal/storage.

Several advantages associated with this invention can be easily seen from the above mentioned example.

Multiple targeted DNA molecules can be measured concurrently. Since liquid from reservoir 51 is fragmented into sample droplets S, each sample droplet S can be mixed with a different PCR premix and conducted to a different test site on the device to allow concurrent measurement of multiple DNA molecules in a single sample without cross-contamination.

For similar reasons just described, the same targeted DNA molecule in multiple samples or multiple DNA molecules in multiple samples can be measured concurrently.

The invention claimed is:

1. An apparatus for temperature cycling, comprising a) an electrowetting-based microfluidic device, the device comprising a substrate plate and a cover plate, wherein the substrate plate and the cover plate define a space in-between, a first array of elongated control electrodes disposed in the substrate plate at a first height from the surface of the substrate plate, and a second array of elongated control electrodes disposed in the substrate plate at a second height from the substrate plate wherein the first and the second arrays are electrically isolated from each other and the second height is larger than the first height and wherein the elongated control electrodes of the first array are substantially perpendicular to the elongated control electrodes of the second array;

b) a first temperature control element and a second temperature control element wherein the electrowetting-based microfluidic device is sandwiched inbetween; and wherein the second temperature control element substantially lines up with the first temperature control element; and c) a set of electric connections to the first and the second temperature control elements for providing electrical currents to the temperature control elements.

2. The apparatus according to claim 1 wherein at least a portion of the first temperature control element is in thermal contact with the electrowetting-based device.

3. The apparatus according to claim 1 wherein at least a portion of the second temperature control element is in thermal contact with the electrowetting-based device.

4. An apparatus for temperature cycling, comprising:

a) an electrowetting-based microfluidic device, the device comprising a substrate plate and a cover plate, wherein the substrate plate and the cover plate define a space in-between, a first array of elongated control electrodes disposed in the substrate plate at a first height from the surface of the substrate plate, and a second array of elongated control electrodes disposed in the substrate plate at a second height from the substrate plate wherein the second height is larger than the first height, the first and the second arrays are electrically isolated from each other and the elongated control electrodes of the first array are substantially perpendicular to the elongated control electrodes of the second array;

b) one temperature control element residing on a first side of the electrowetting-based microfluidic device and in thermal communication with the device; and c) one electric connection to the temperature control element for providing electrical current to the temperature control element.

5. The apparatus according to claim 4 wherein at least a portion of the temperature control element is in thermal contact with the electrowetting-based microfluidic device.

6. The apparatus of claim 1 wherein the first temperature control element comprises a first set of temperature control elements.

7. The apparatus of claim 1 wherein the second temperature control element comprises a second set of temperature control elements.

8. The apparatus of claim 4 wherein the one temperature control element comprises a set of temperature control elements.

9. The apparatus of claim 4 wherein the one electric connection comprises a set of electric connections.

10. The apparatus of claim 1 wherein substantially perpendicular is perpendicular.

11. The apparatus of claim 4 wherein substantially perpendicular is perpendicular.

* * * * *